United States Patent [19]

Provost

[11] Patent Number: 4,468,197
[45] Date of Patent: Aug. 28, 1984

[54] APPARATUS AND METHOD FOR DETECTING CAVITIES

[76] Inventor: Wayne Provost, 2541 Neffs Cir., Salt Lake City, Utah 84109

[21] Appl. No.: 488,676

[22] Filed: Apr. 26, 1983

[51] Int. Cl.³ .............................................. A61B 1/24
[52] U.S. Cl. ................................................... 433/30
[58] Field of Search .................... 433/29, 229, 228, 30

[56] References Cited

U.S. PATENT DOCUMENTS

| | | | |
|---|---|---|---|
| 2,840,070 | 6/1958 | Tofflemire | 128/11 |
| 3,152,587 | 10/1964 | Ullrich et al. | 128/2 |
| 4,077,399 | 3/1978 | Le Roy | 128/23 |
| 4,265,227 | 5/1981 | Ruge | 128/23 |
| 4,286,602 | 9/1981 | Guy | 128/665 |
| 4,290,433 | 9/1981 | Alfano | 433/25 |
| 4,324,546 | 4/1982 | Heitlinger | 433/25 |

OTHER PUBLICATIONS

G. R. Winter et al., "Transillumination in the Oral Cavity," Dental Digest 106–109 (Mar. 1949).
R. C. Taylor et al., "Illumination of the Oral Cavity," 74 JADA 1207–1209 (May 1967).
J. Friedman et al., "Transillumination of the Oral Cavity with Use of Fiber Optics," 80 JADA 801–809 (Apr. 1970).
J. L. Bomba, "Fiber Optic Lighting Systems: Their Role in Dentistry," 15 Dental Clinics of North America 197–218, No. 1 (Jan. 1971).
J. Barenie et al., "The Use of Fiber Optics Transillumination for the Detection of Proximal Caries," 36 Oral Surg. 891–897, No. 6 (Dec. 1973).
"Discover the World of Demetron," an Advertising brochure of Demetron Research Corporation, Danbury, Conn. (believed to have been published about Apr. 1983).

Primary Examiner—Robert Peshock
Attorney, Agent, or Firm—H. Ross Workman; Rick D. Nydegger; Dale E. Hulse

[57] ABSTRACT

An apparatus for detecting interproximal cavities and the like. A high intensity light from an incandescent lamp is transmitted through an optical fiber bundle and is projected onto a tooth. Light passing around or through said tooth is detected by a second optical fiber bundle and is transmitted to a viewer where it is projected through a lense system onto an opaque screen where an image of the tooth can be viewed and any defects therein can be detected.

18 Claims, 4 Drawing Figures

APPARATUS AND METHOD FOR DETECTING CAVITIES

BACKGROUND

1. Field of the Invention

The present invention relates to apparatus and methods for detecting cavities and, more particularly, to a novel apparatus and method which utilizes a high intensity, visible light to detect interproximal cavities.

2. The Prior Art

In order for a dentist to provide adequate dental care for his patients, it is necessary that he identify and treat all cavities and other serious defects which are associated with the teeth. However, a significant portion of all teeth are unobservable during a clinical examination. For example, interproximal cavities which occur in the proximal surfaces of adjacent teeth are invisible to a dentist when he performs a visual examination.

With the development of the hot-cathode x-ray tube in 1913, x-rays became an effective means for detecting interproximal cavities and other hidden defects. By 1940, x-rays had come into general use in dentistry. It has been estimated that about 100,000 x-ray generators are in use today in dental offices throughout the United States. In most developed countries today, a radiographic survey of the mouth using x-rays to detect interproximal cavities and other defects is considered an essential part of a thorough dental examination.

In spite of the usefulness of x-rays as a diagnostic tool, there is still a substantial amount of apprehension concerning their use. As with any type of radiation, x-ray exposure can cause various types of unwanted biological consequences to both the patient, and the dentist or technician who is operating the equipment. For example, very large doses of radiation can cause destruction and necrosis of body tissue. Latent effects such as leukemia, cancer, life shortening and genetic defects in offspring can also be caused by radiation.

Thus, those familiar with the potential problems of radiation suggest that the use of x-rays for diagnostic purposes be kept to a minimum. Indeed, many studies have been undertaken to identify safe limits of radiation and numerous procedures have been outlined by various health organizations to try and reduce radiation exposure. However, the ultimate decision to utilize x-rays must be made by a professional on an individual basis wherein the expected yield of diagnostic information can be balanced against the element of biologic risk.

In addition to unwanted biological consequences, there are additional problems associated with the use of x-rays to detect interproximal cavities. For example, the x-ray equipment is generally placed in a separate room. Hence, a patient must first be taken to that room to have the radiographs prepared and must then be moved to another room for further examination and treatment. Additionally, there is a time delay between taking the radiographs and the time at which they can be examined. The x-ray film must be developed before the results can be seen. Hence, if the radiographs do not turn out or if they show the wrong views, the patient must be returned to the x-ray room. Also, because of the delays in developing x-ray film, dentists and technicians are often tempted to overexpose and underdevelop the film to shorten the process. However, this unnecessarily exposes the patient to higher levels of radiation.

In view of the foregoing, it is apparent that it would be a significant and indeed, perhaps a revolutionary advancement in the art to provide an instrument and method whereby interproximal cavities and other hidden defects could be detected without exposing the patient and dentist to the biological risks which are associated with the use of x-rays. Such a device and method are disclosed and claimed herein.

OBJECTS AND BRIEF SUMMARY OF THE INVENTION

It is a primary object of the present invention to provide an apparatus and method for detecting cavities such as interproximal cavities without the use of harmful radiation such as x-rays.

It is a further object of the present invention to provide an apparatus and method for detecting interproximal cavities which utilizes a high intensity, visible light.

It is still another object of the present invention to provide an apparatus and method for detecting interproximal cavities wherein the dentist can instantaneously see the results of the examination.

It is another object of the present invention to provide an apparatus for detecting interproximal cavities wherein the apparatus is compact and portable and is relatively inexpensive when compared to the cost of x-ray equipment.

In accordance with the foregoing objects, the present invention provides an apparatus and method for detecting interproximal cavities which utilizes a high intensity, visible light and a system of optical fibers to detect interproximal cavities without the use of harmful radiation.

In one preferred embodiment, high intensity light, such as from a halogen projection lamp, is transmitted through an optical fiber bundle into a small hand piece which can be positioned in a patient's mouth. The hand piece has a mouthpiece attached to the distal end which is generally U-shaped in cross-section such that it can be positioned over both sides of one or more teeth. The light transmitted through the optical fiber is reflected by means of a mirror or prism in one of the legs of the U-shaped portion of the mouthpiece such that the light is projected towards the second leg of the mouthpiece. When the device is positioned over a tooth, a portion of the light which is projected from the first leg of the mouthpiece strikes the tooth. Most of this light is either reflected or absorbed. However, a portion of the light is transmitted through the tooth and is reflected by means of a mirror or prism in the second leg of the mouthpiece to a coherent optical fiber bundle which transmits this light back to a detection device.

The detection device of the present invention utilizes a series of lenses to focus the light transmitted through the coherent fiber bundle onto a small opaque glass screen where an image representing the structure of the tooth can be observed. Defects such as interproximal cavities appear as light spots on the image which is projected on the opaque screen. Thus, by moving the mouthpiece such that it is positioned over various portions of the teeth, a dentist can detect interproximal cavities and other similar defects.

In a second preferred embodiment of the present invention, a camera is provided with the detection device such that a permanent photographic record of the images which are projected onto the opaque screen can be recorded.

Accordingly, the present invention provides an apparatus and means whereby interproximal cavities can be detected by a dentist without the use of harmful radiation and whereby he can instantaneously view the results of the examination.

BRIEF DESCRIPTION OF THE DRAWINGS

Reference is next made to the drawings, in which like parts are designated with like numerals throughout, and in which.

DETAILED DESCRIPTION OF THE PREFERRED EMBODIMENTS

Figure 1:
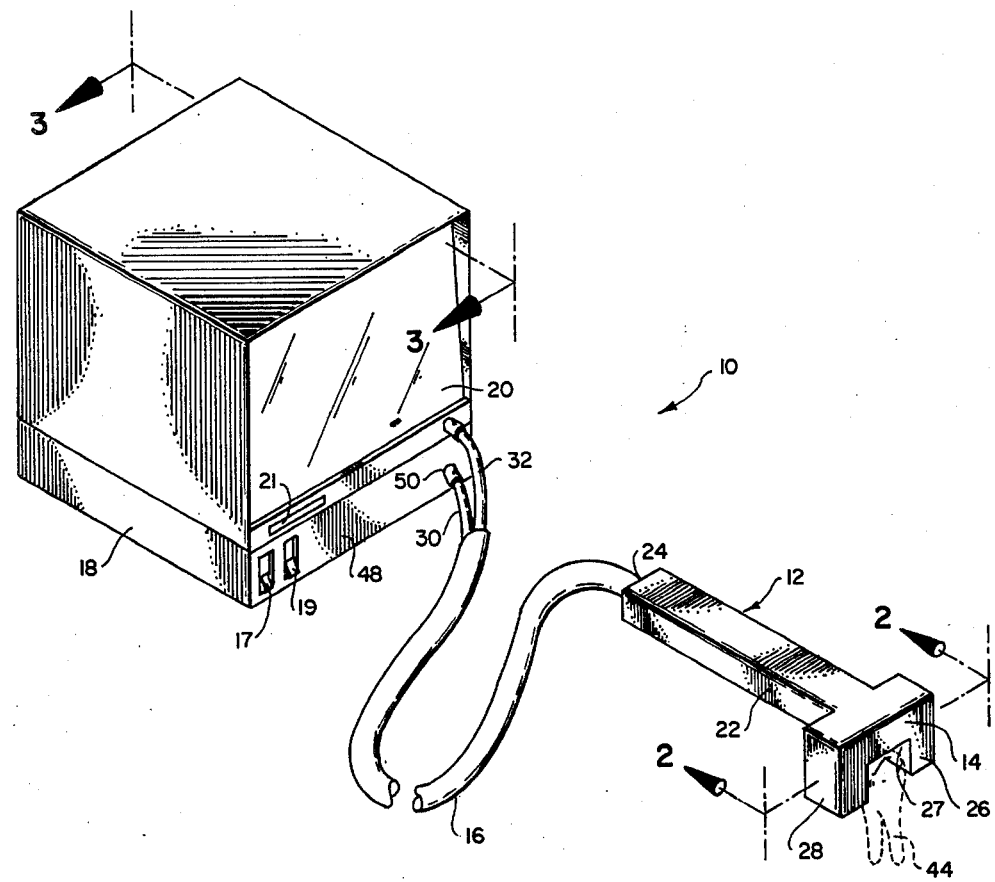
FIG. 1 is a perspective view of a first preferred embodiment of a cavity detecting apparatus constructed in accordance with the present invention.

Reference is first made to FIG. 1 wherein a cavity detector constructed in accordance with the present invention is illustrated and is generally designated at 10. Cavity detector 10 comprises a hand piece 12 having a handle 22 and a U-shaped mouthpiece 14 on the distal end thereof such that it can be positioned over the various teeth within a patient's mouth. Hand piece 12 is connected to a power source 18 and viewer 20 by means of cable 16 which encases optical fiber bundles 30 and 32.

Figure 2:
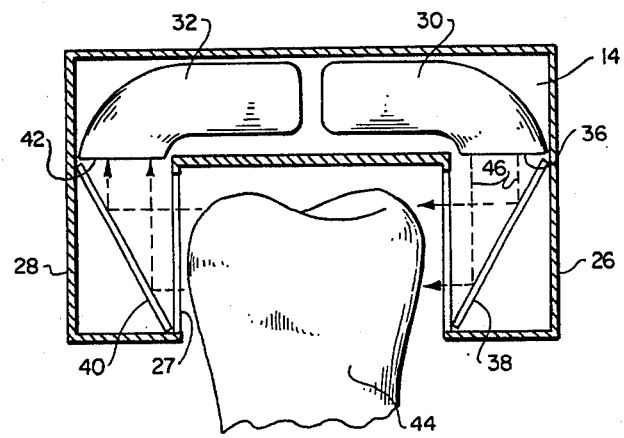
FIG. 2 is a cross-sectional view of the distal portion of the handpiece taken at the position indicated by line 2—2 of FIG. 1.

In the preferred embodiment illustrated in FIG. 1, hand piece 12 includes an elongated handle 22 having an opening formed in the proximal end 24 thereof into which cable 16 is inserted. The handle 22 is designed to provide a comfortable, efficient means for the dentist to control the placement of mouthpiece 14 in a patient's mouth. Mouthpiece 14 is positioned on the distal end of handle 22 and is U-shaped, having downwardly projecting legs 26 and 28. The space 27 between legs 26 and 28 of mouthpiece 14 is designed such that it can accommodate a tooth 44 (see also FIG. 2). Thus, as will be more fully discussed hereinafter, mouthpiece 14 can be positioned over a row of teeth and moved from tooth to tooth to enable the dentist to examine all of the teeth and the spaces in-between.

Referring again to FIG. 1, cable 16 is formed from a length of plastic or other flexible tubing and encases the two optical fiber bundles 30 and 32. Optical fiber bundle 30 is connected to power source 18 and transmits light produced therein to mouthpiece 14 where it is projected onto tooth 44 (see FIG. 2). The light which passes through and around tooth 44, is ultimately detected by optical fiber bundle 32, and is transmitted back through cable 16 to viewer 20.

In the embodiment illustrated in FIG. 1, optical fiber bundles 30 and 32 are enclosed within the cable 16 from hand piece 12 to a point just before their ends where they are connected to power source 18 and viewer 20. Accordingly, there is only one line extending from the power source and viewer to the hand piece instead of two, thus reducing the likelihood that the optical fiber bundles will become entangled with other equipment. Additionally, the casing of cable 16 provides additional protection to the fragile optical fibers.

Power source 18 produces the light which is transmitted by fiber bundle 30 to mouthpiece 14 and is provided with two switches 17 and 19 to control the light. Switch 17 is a power switch and is used to turn a lamp 54 (see FIG. 3) on and off. Switch 19 is used to control the intensity of the light which is produced between a high and low value. Thus, a brighter light can be used for larger, denser teeth while a dimmer light can be used for smaller teeth.

Referring again to FIG. 2, the means whereby the light is transmitted through mouthpiece 14 to detect cavities in tooth 44 is illustrated in greater detail. As discussed previously, optical fiber bundle 30 from power source 18 passes through cable 16 and into handle 22 of hand piece 12 where it extends into mouthpiece 14. In the preferred embodiment the distal end 36 of optical fiber bundle 30 is positioned such that it points downwardly into leg 26 of mouthpiece 14. A mirror 38 is positioned in the bottom of leg 26 such that the light which is emitted from distal end 36 is reflected as illustrated by dotted lines 46 and shines on tooth 44 which is positioned within space 27 of mouthpiece 14.

Although tooth 44 is generally opaque, a portion of the light emitted from optical fiber bundle 30 and reflected by mirror 38 passes through or around tooth 44. The amount of light which passes through the tooth is dependent upon the thickness and density of the tooth at that particular location. Thus, if a cavity is present in tooth 44, the void space which it creates allows more light to pass through this portion of the tooth than would normally be expected.

The light passing through and around tooth 44 is reflected by mirror 40 in leg 28 of mouthpiece 14 and is picked up by the distal end 42 of optical fiber bundle 32. The light is then transmitted by optical fiber bundle 32 back to viewer 20. As will be more fully discussed hereinafter, it is important that optical fiber bundle 32 which picks up the light transmitted through tooth 44 be a coherent optical fiber bundle.

Although the distal ends 36 and 42 of optical fiber bundles 30 and 32 are illustrated as pointing downward such that light can be reflected off mirrors 38 and 40, it will be readily appreciated that other configurations and other systems such as the use of prisms could also be utilized to achieve the same effect.

Figure 3:
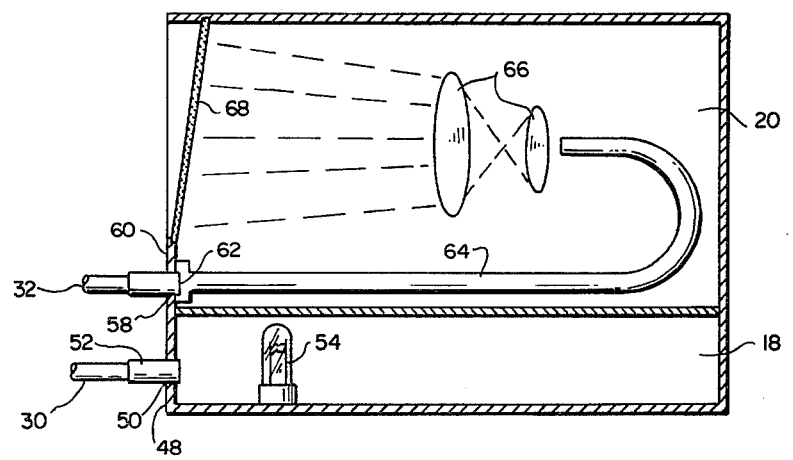
FIG. 3 is a cross-sectional view of the control unit taken at the position indicated by line 3—3 of FIG. 1.

Referring now to FIG. 3, the power source and viewer of FIG. 1 are shown in cross-section to more fully illustrate the manner in which they operate. Located in the forward face 48 of power source 18 is an outlet 50 (see also FIG. 1). The proximal end 52 of optical fiber bundle 30 is inserted into outlet 50. A high intensity lamp 54 is positioned within power source 18 such that the output from lamp 54 is projected onto proximal end 52 of optical fiber bundle 30.

In the preferred embodiment, lamp 54 comprises a high intensity incandescent lamp such as used in various types of movie or slide projectors. It will also be appreciated by those skilled in the art that other types of light sources which produces a visible light could also be utilized. For example, monocromatic lights such as certain types of lasers could also be utilized provided that they produce a high intensity visible light but are not so intense that they can cause tissue damage. While the preferred embodiment utilizes an incandescent lamp, this is intended to merely be by way of example and not restrictive. Any light within the visible range is intended to be within the scope of the present invention.

In the embodiment illustrated in FIGS. 1 and 3, viewer 20 is shown positioned directly above power source 18. However, it will readily be appreciated by those skilled in the art that viewer 20 could also comprise a separate unit such that it could be moved to other positions.

An inlet 58 is formed in the forward face 60 of viewer 20. The proximal end 62 of optical fiber bundle 32 is inserted into inlet 58. The image transmitted by optical fiber bundle 32 is then carried by an optical fiber bundle 64 where it is projected through a series of lenses 66 onto a small opaque screen 68 positioned in forward face 60 of viewer 20. Screen 68 provides a means for the dentist to view an image of the teeth and can be formed of either opaque glass or opaque plastic. The size of screen 68 can vary from two or three inches square to several times that size. While larger screens provide a larger image to examine, they require more room and some clarity is lost in magnification. Thus, smaller screens are generally preferred, provided that the image projected thereon is large enough to be readily examined.

As mentioned previously, optical fiber bundle 32 and also bundle 64 must be coherent bundles. That is, the arrangement of the ends of the individual fibers at one end of the bundles must be identical to the arrangement at the other end. Inasmuch as bundle 32 is transmitting an image and not just light, the orientation of the fibers must be consistent; otherwise, the image will be distorted.

A focus control nob 21 (see FIG. 1) is provided on the front of viewer 20 to provide a means for adjusting the lense system 66 to obtain a clear image.

Figure 4:
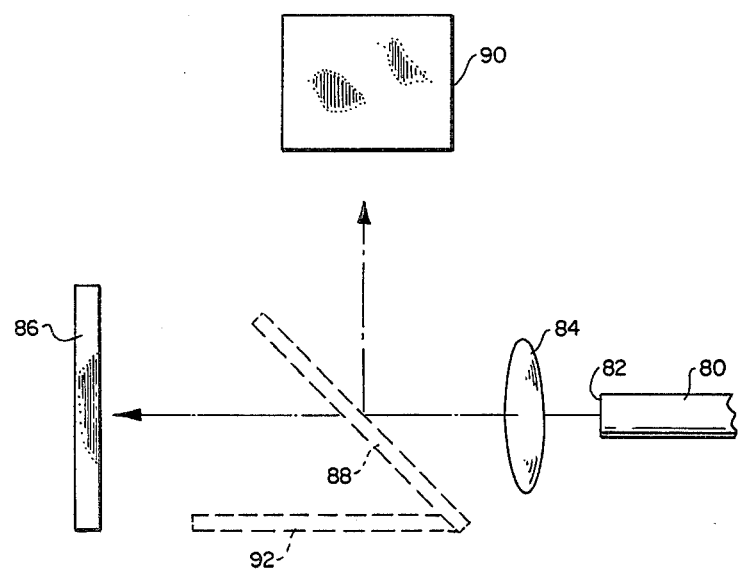
FIG. 4 is a schematic block diagram illustrating a second embodiment of a detection unit constructed in accordance with the present invention which incorporates a camera for making a permanent record of the image produced by the present invention.

Referring now to FIG. 4, a second preferred embodiment of the viewer portion of the present invention is illustrated in a schematic block diagram. The image from the mouthpiece is transmitted to the viewer through a coherent optical fiber bundle 80. The image projected from the end 82 of optical fiber bundle 80 is focussed through a lense system 84 and is projected either onto an opaque screen 86 or is reflected by means of a mirror 88 into a camera 90. It is often times desirable for a dentist to make a permanent record of cavities which he detects for his files. Thus, the present invention can be equipped with an instant camera 90 to make such a permanent record.

Normally, mirror 88 is positioned in the lower position as indicated by dotted lines 92 such that the image projected through lense 84 is focussed onto screen 86 where it can be viewed by the dentist. However, mirror 88 is rotatable such that it can be positioned in the path of the projected image to reflect the image to a camera 90 positioned on top of the viewer. It will of course be readily apparent to those skilled in the art that many additional configurations and systems could also be utilized to achieve the same desired effect. For example, camera 90 can be positioned such that it takes a picture of the image projected onto screen 86 rather than having the image projected directly into the camera. Alternatively, a series of prisms or partially coated mirrors could be utilized to simultaneously project the image onto the opaque screen and into the camera.

From the foregoing, it will be apparent to those skilled in the art that the present invention provides a novel apparatus for detecting interproximal cavities which is simple in its construction and is easy to use. Additionally, because the present apparatus utilizes a visible light such as incandescent light to detect the cavities, the patient and dentist are not subjected to the harmful radiation associated with x-rays.

The method of utilizing the apparatus of the present invention to detect interproximal cavities will be readily apparent to those of ordinary skill in the art.

Power system 18 is connected to a source of electrical power such as a standard 110 volt electrical outlet and switch 17 is turned on such that lamp 54 produces a high intensity light. The light produced by lamp 54 is transmitted through optical fiber bundle 30 in cable 16 and into hand piece 12. The light is projected through the distal tip 36 of optical fiber bundle 30 onto mirror 38 where it is reflected out into space 27 in mouthpiece 14.

Mouthpiece 14 can then be placed in a patient's mouth over his teeth. The light which is reflected out of mouthpiece 14 strikes any teeth which are positioned in space 27. Much of the light is absorbed by the teeth and surrounding tissue. However, a portion of the light passes through or around the teeth. This portion of light which passes through or around the teeth is reflected by means of mirror 40 onto the distal end 42 of optical fiber bundle 32 and is transmitted back to viewer 20. The image transmitted through optical fiber bundle 32 is projected through the lens system 66 and onto screen 68 where it can be viewed by the dentist.

Normally, teeth will appear as a dark image on a screen 68. However, cavities or other defects which change the density of the teeth will either lighten or darken the image projected onto screen 68. Thus, the dentist is able to see those areas in which defects are located. Depending upon the size and density of the teeth, the dentist can change the intensity of the light between high and low values by utilizing the switch 19 on power source 18. This allows the dentist to obtain a clear image regardless of whether the teeth are large or small, thick or thin.

End piece 12 is designed such that it can easily be held by the dentist to position mouthpiece 14 within the mouth of the patient. The opening 27 between legs 26 and 28 of mouthpiece 14 is sized such that it can easily accommodate teeth of varying sizes. When mouthpiece 14 is positioned within a patient's mouth over the teeth, it can be moved along the row as the dentist examines the images projected onto the screen of the viewer. When the dentist notes any irregularity, he can either make a notation on the patient's chart or, if the apparatus is equipped with a camera, he can take a picture to make a permanent record of the projected images. Mouthpiece 14 is slowly moved around the entire row of teeth such that the dentist can examine all of the teeth and the spaces therebetween. The apparatus and method of the present invention can be used on both the upper and lower teeth.

From the foregoing description, it will be readily apparent that the apparatus of the present invention provides a means for detecting interproximal cavities which eliminates many of the problems associated with the prior art devices and techniques. The present invention does not utilize x-rays or other forms of radiation which can be harmful to both the patient and the dentist or his technicians. Additionally, the present invention provides a means whereby the dentist can view the results as the examination occurs and can easily recheck any areas about which he may have questions.

Additionally, the examination can take place in the chair in which the dentist performs the other procedures on the patient's mouth so that the patient does not have to be moved from room to room. Further, because of its relatively small size, the present invention can easily be utilized at locations other than the dentist's office to provide screening examinations to large groups of people.

While the present invention has been described with reference to the presently preferred embodiments, it will be readily appreciated that the invention may be embodied in other specific forms without departing from its spirit or essential characteristics. The described embodiments are, therefore, to be considered in all respects as illustrative and not restrictive, and the scope of the invention is thus indicated by the appended claims rather than by the foregoing description. All modifications or changes which come within the meaning and range of equivalency of the claims are to be embraced within their scope.

What is claimed and desired to be secured by United States Letters Patent is:

1. An apparatus for detecting cavities, said apparatus comprising:
   a light source which produces a high intensity visible light;
   means for projecting the light from the light source onto a tooth;
   means for receiving light transmitted through the tooth; and
   means for producing an image of the transmitted light received so as to provide an image of the tooth.

2. An apparatus for detecting cavities as defined in claim 1 wherein said light source comprises an incandescent lamp.

3. An apparatus for detecting cavities as defined in claim 1 wherein the means for projecting light from the light source comprises a first optical fiber bundle.

4. An apparatus for detecting cavities as defined in claim 3 wherein the means for projecting light from the light source further comprises a mouthpiece connected to the end of said first optical fiber bundle, said mouthpiece being configurated such that it can be positioned over a tooth in a patient's mouth.

5. An apparatus for detecting cavities as defined in claim 4 wherein the means for receiving light transmitted through the tooth comprises a second optical fiber bundle connected to said mouthpiece, said second optical fiber bundle being a coherent bundle and said second optical fiber bundle serving to transmit the received light to the image producing means.

6. An apparatus for detecting cavities as defined in claim 5 wherein the image producing means comprises an opaque screen positioned in front of a proximal end of said second optical fiber bundle.

7. An apparatus for detecting cavities as defined in claim 6 wherein the opaque screen is mounted within a viewer unit.

8. An apparatus for detecting cavities as defined in claim 7 wherein the viewer unit further comprises a lense system positioned between the opaque screen and the proximal end of the second optical fiber bundle, said lense system serving to focus the light transmitted by the second optical fiber bundle onto said opaque screen.

9. An apparatus for detecting cavities as defined in claim 8 wherein said viewer unit further comprises a camera for making a permanent record of the light transmitted through the second optical fiber bundle.

10. An apparatus for detecting interproximal cavities, said apparatus comprising:
    an incandescent light source for producing a high intensity visible light;
    a first optical fiber bundle for receiving and transmitting said high intensity light;
    a mouthpiece for directing said high intensity light from said first optical fiber bundle onto a tooth in a patient's mouth, said mouthpiece being attached to a distal end of said first optical fiber bundle;
    a second optical fiber bundle having a distal end thereof positioned in said mouthpiece to receive light transmitted through said tooth; and
    means for imaging the light received by said second optical fiber bundle.

11. An apparatus for detecting interproximal cavities as defined in claim 10 wherein said imaging means comprises an opaque screen positioned in front of a proximal end of said second optical fiber bundle.

12. An apparatus for detecting interproximal cavities as defined in claim 11 wherein the imaging means further comprises a lense system positioned between the opaque screen and the proximal end of the second optical fiber bundle, said lense systm serving to focus images displayed on said opaque screen.

13. An apparatus for detecting interproximal cavities as defined in claim 12 wherein the imaging means further comprises a camera for making a permanent record of the light received by said second optical fiber bundle.

14. A method for detecting cavities, said method comprising the steps of:
    projecting a high intensity light onto a tooth;
    receiving at least a portion of the light which passes through said tooth; and
    forming a visible image from the received portion of light so as to detect any cavities in the tooth.

15. A method for detecting cavities as defined in claim 14 wherein the forming step comprises projecting the light which is received onto an opaque screen.

16. A method for detecting cavities as defined in claim 15 wherein the forming step further comprises taking a photograph of the image which is produced by the received light to form a permanent record.

17. A method for detecting cavities as defined in claim 14 wherein the projecting step comprises producing a light by an incandescent lamp and transmitting said light to the tooth through an optical fiber bundle.

18. A method for detecting cavities as defined in claim 14 wherein the receiving step comprises receiving light passing through said tooth into an optical fiber bundle, the optical fiber bundle transmitting the received light to an imaging means.

* * * * *

UNITED STATES PATENT AND TRADEMARK OFFICE
CERTIFICATE OF CORRECTION

PATENT NO. : 4,468,197
DATED : August 28, 1984
INVENTOR(S) : Wayne Provost

It is certified that error appears in the above—identified patent and that said Letters Patent is hereby corrected as shown below:

Column 4, line 62, "produces" should be --produce--
Column 4, line 63, "monocromatic" should be --monochromatic--
Column 5, line 44, "often times" should be --oftentimes--
Column 8, line 31, "systm" should be --system--

Signed and Sealed this

Fifth Day of March 1985

[SEAL]

*Attest:*

DONALD J. QUIGG

*Attesting Officer*  *Acting Commissioner of Patents and Trademarks*